(12) United States Patent
Brandon

(10) Patent No.: US 8,894,694 B2
(45) Date of Patent: Nov. 25, 2014

(54) LOCKING PLATES HAVING GUIDED LOCKING SCREWS AND METHODS THEREFOR

(76) Inventor: Mark Leonard Brandon, Staten Island, NY (US)

(*) Notice: Subject to any disclaimer, the term of this patent is extended or adjusted under 35 U.S.C. 154(b) by 0 days.

(21) Appl. No.: 13/218,485

(22) Filed: Aug. 26, 2011

(65) Prior Publication Data

US 2012/0071934 A1 Mar. 22, 2012

Related U.S. Application Data

(60) Provisional application No. 61/377,170, filed on Aug. 26, 2010.

(51) Int. Cl.
| | | |
|---|---|---|
| *A61B 17/80* | (2006.01) | |
| *A61B 17/17* | (2006.01) | |
| *A61B 17/16* | (2006.01) | |
| *A61B 17/86* | (2006.01) | |
| *A61B 19/00* | (2006.01) | |

(52) U.S. Cl.
CPC ......... *A61B 17/1728* (2013.01); *A61B 17/1615* (2013.01); *A61B 17/1796* (2013.01); *A61B 17/80* (2013.01); *A61B 17/8047* (2013.01); *A61B 17/8605* (2013.01); *A61B 17/8625* (2013.01); *A61B 17/864* (2013.01); *A61B 2019/307* (2013.01); *A61B 2019/462* (2013.01)
USPC .................. 606/286; 606/87; 606/96

(58) Field of Classification Search
USPC ............ 606/70–71, 280–299, 86 A, 86 B, 96, 606/104, 915, 916; 227/15, 119; 173/29, 173/132; 408/241 G, 72 R, 112
See application file for complete search history.

(56) References Cited

U.S. PATENT DOCUMENTS

| | | | | |
|---|---|---|---|---|
| 5,127,914 | A | * | 7/1992 | Calderale et al. ............... 606/65 |
| 5,474,553 | A | * | 12/1995 | Baumgart .................... 606/71 |
| 6,129,730 | A | * | 10/2000 | Bono et al. .................... 606/291 |
| 6,436,103 | B1 | * | 8/2002 | Suddaby ...................... 606/96 |
| 7,278,997 | B1 | * | 10/2007 | Mueller et al. ............... 606/104 |
| 8,425,573 | B2 | * | 4/2013 | Erickson et al. .............. 606/281 |
| 8,623,019 | B2 | * | 1/2014 | Perrow et al. ................. 606/70 |
| 2002/0156474 | A1 | * | 10/2002 | Wack et al. .................... 606/69 |
| 2003/0208204 | A1 | * | 11/2003 | Bailey et al. ................... 606/69 |
| 2004/0181227 | A1 | * | 9/2004 | Khalili ......................... 606/69 |
| 2005/0159711 | A1 | * | 7/2005 | Kathrani et al. .............. 604/264 |
| 2005/0234472 | A1 | * | 10/2005 | Huebner ....................... 606/104 |
| 2006/0116679 | A1 | * | 6/2006 | Lutz et al. ..................... 606/69 |
| 2006/0161158 | A1 | * | 7/2006 | Orbay et al. .................. 606/69 |
| 2007/0053765 | A1 | * | 3/2007 | Warnick et al. .............. 411/378 |
| 2009/0228047 | A1 | * | 9/2009 | Derouet et al. ............... 606/286 |
| 2010/0057138 | A1 | * | 3/2010 | Murner et al. ................ 606/308 |
| 2010/0100134 | A1 | * | 4/2010 | Mocanu ....................... 606/281 |
| 2011/0264095 | A1 | * | 10/2011 | Cheng et al. .................. 606/71 |

* cited by examiner

*Primary Examiner* — Todd Manahan
*Assistant Examiner* — Marcela I Shirsat
(74) *Attorney, Agent, or Firm* — Doherty IP Law Group LLC

(57) ABSTRACT

A locking plate system includes a locking plate having a screw hole with an inner diameter and internal threads, and a slot formed in a top surface of the locking plate adjacent the screw hole. The system includes a screw guide having a main body including an upper end and a lower end, and an attachment flange projecting from the lower end of the main body for insertion into the slot. The screw guide includes a central opening having an inner diameter that matches the inner diameter of the screw hole. The system includes a locking screw having external threads extending along the length thereof. The external threads have an outer diameter that matches the inner diameter of the central opening of the screw guide. The locking screw is insertable into the central opening of the screw guide for being directed into the screw hole.

17 Claims, 20 Drawing Sheets

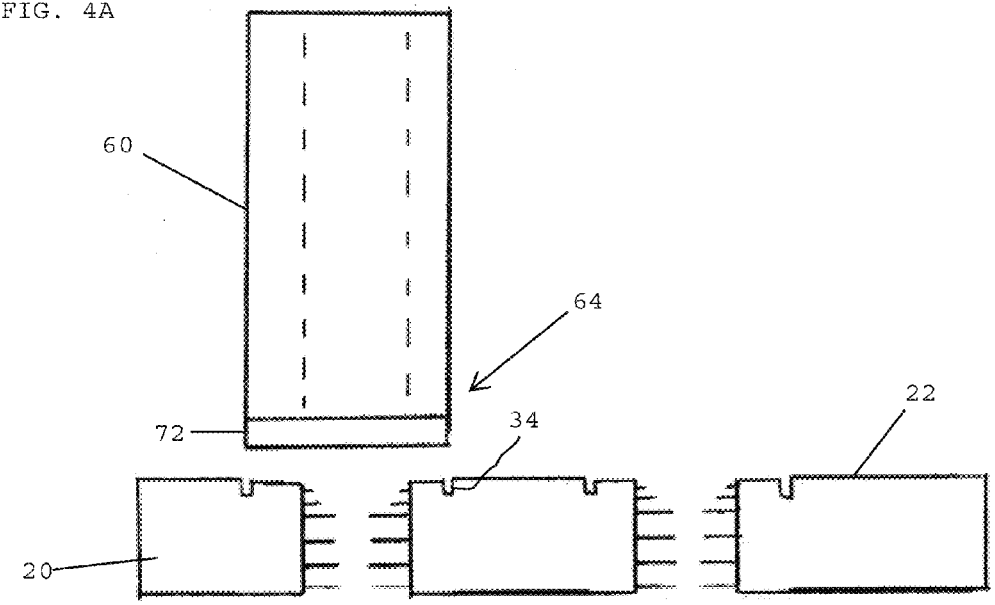
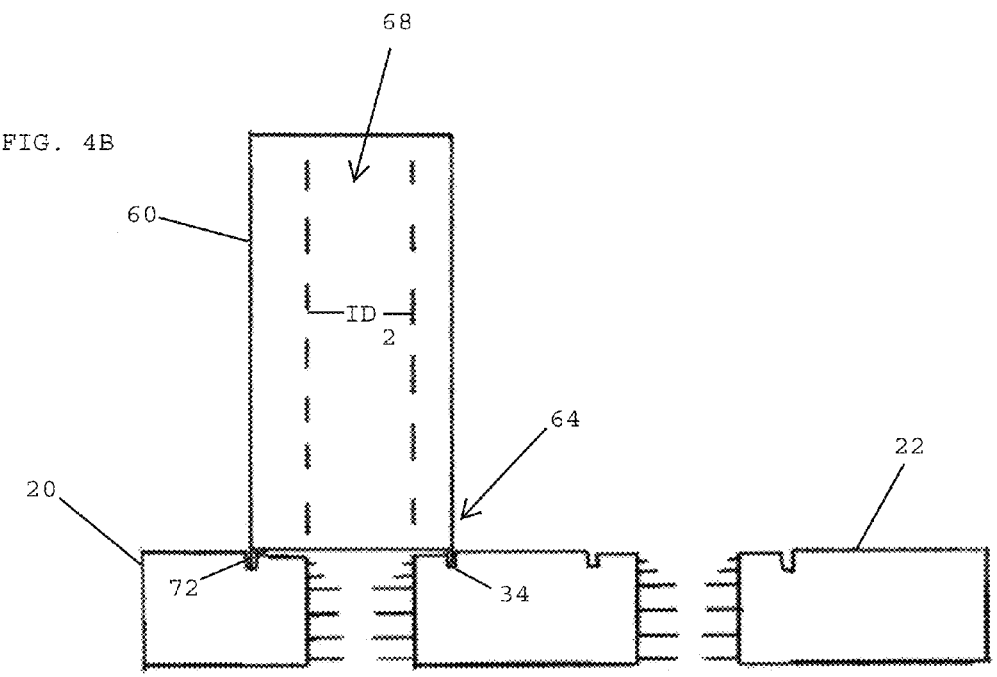

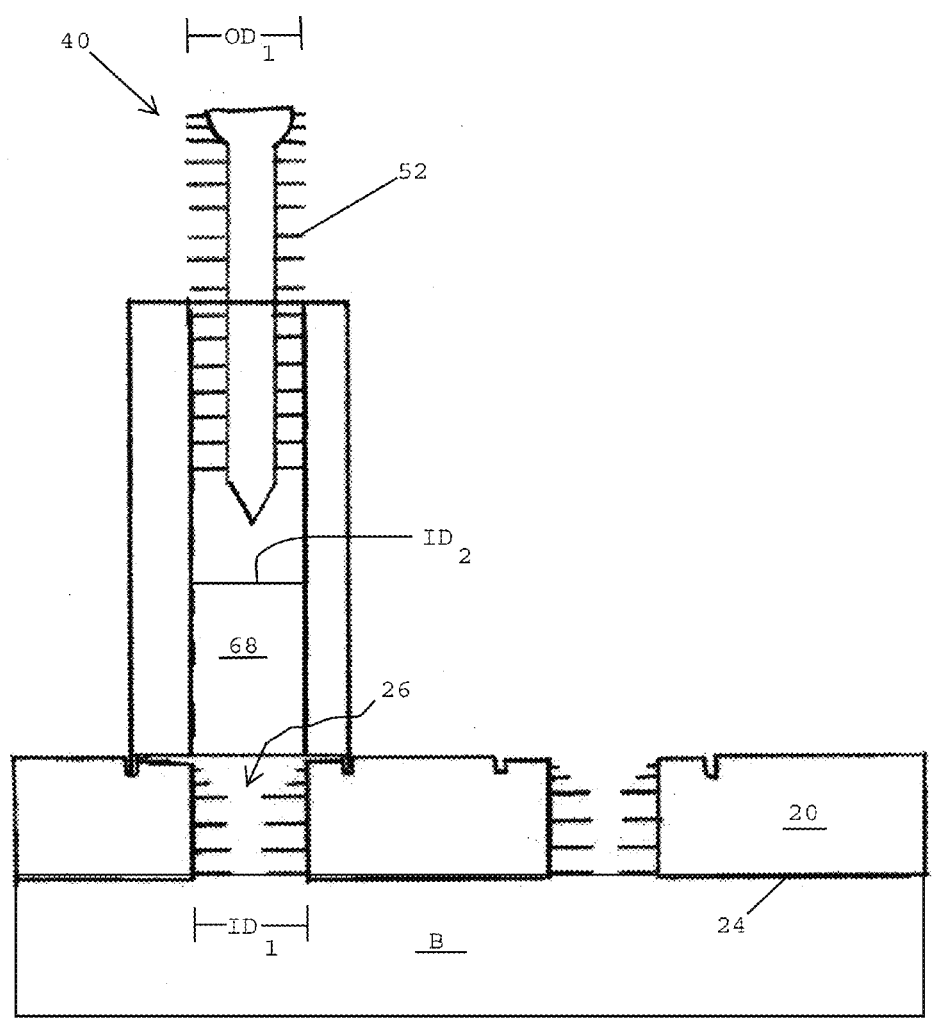

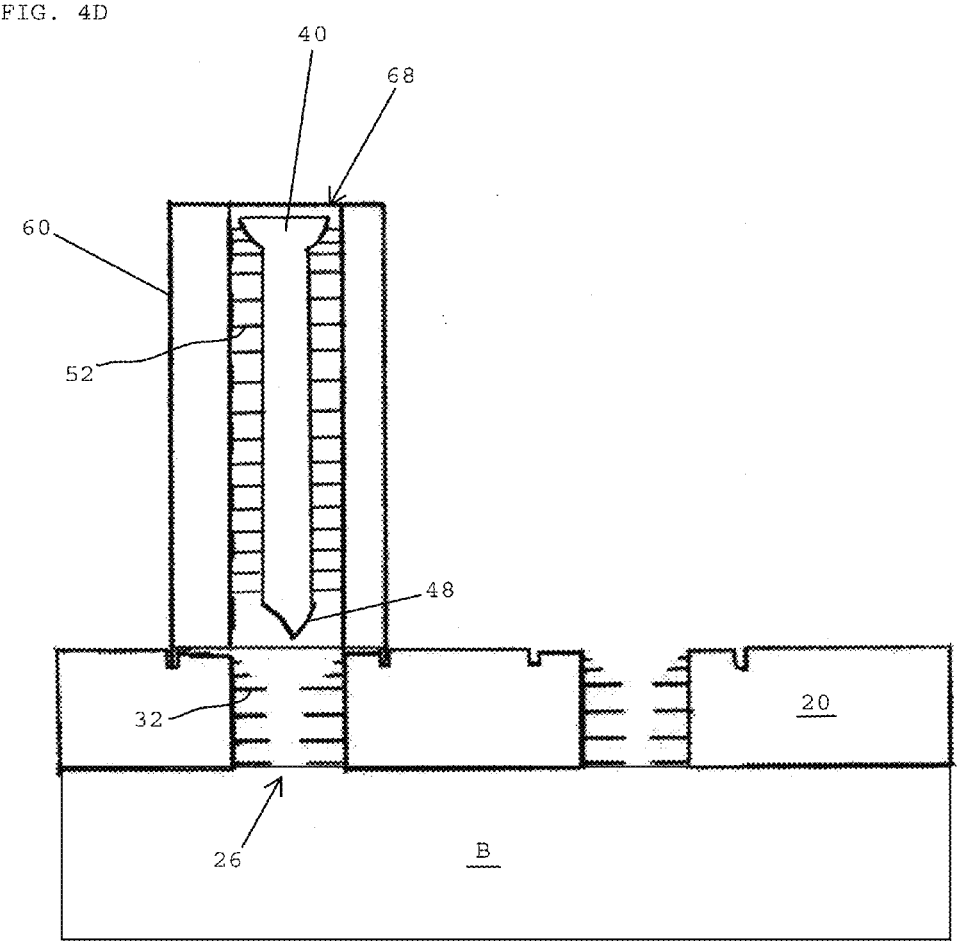

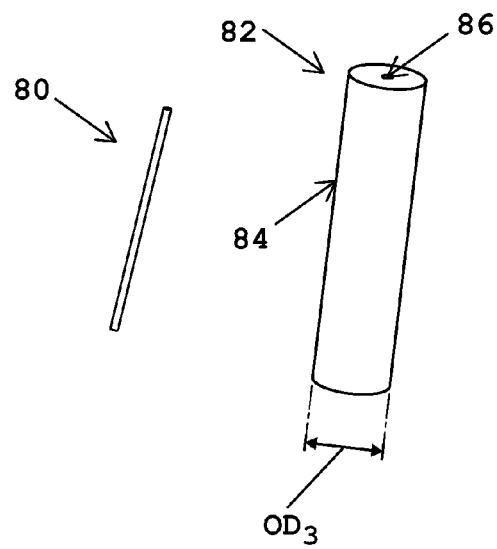
FIG. 5
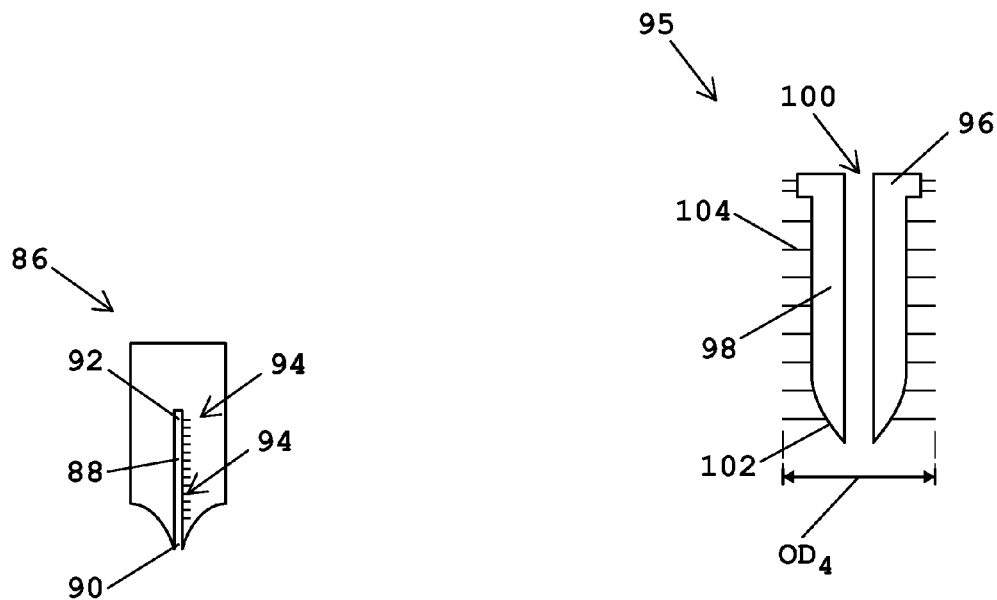
FIG. 6
FIG. 7

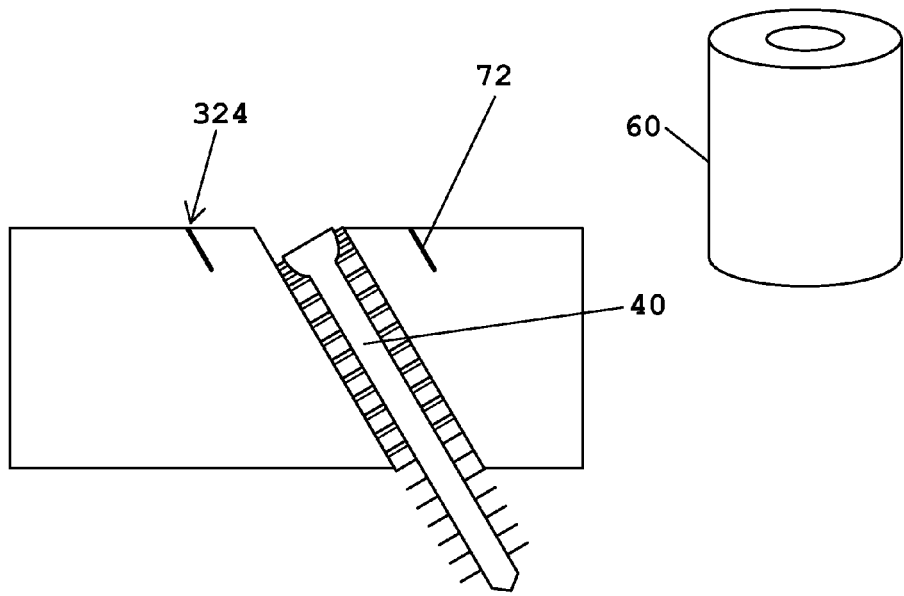
FIG. 11F
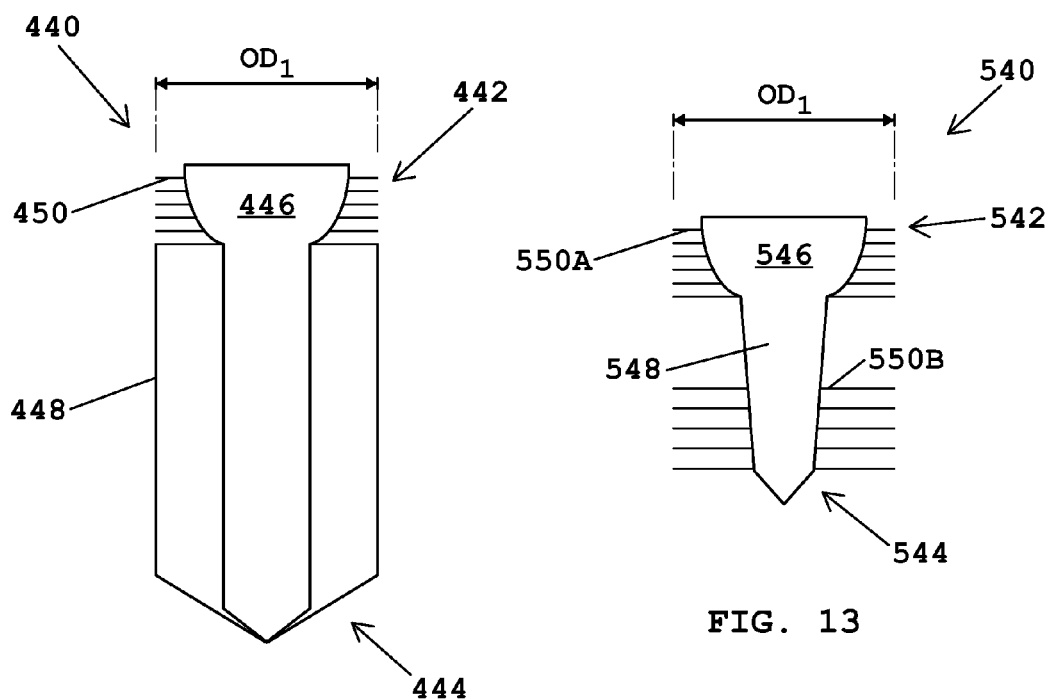
FIG. 12
FIG. 13

LOCKING PLATES HAVING GUIDED LOCKING SCREWS AND METHODS THEREFOR

CROSS-REFERENCE TO RELATED APPLICATIONS

The present application claims the benefit of U.S. Provisional Application Ser. No. 61/377,170, filed Aug. 26, 2010, entitled "Locking Plates Having Guided Locking Screws And Methods Therefor," the disclosure of which is hereby incorporated by reference herein.

BACKGROUND OF THE INVENTION

1. Field of the Invention

The present invention generally relates to bone plates and more specifically relates to bone plates having guided locking screws.

2. Description of the Related Art

Locking plates have been used for many years in the field of orthopedics for repairing bone fractures. Locking plates typically have threaded screw holes that are adapted to receive locking screws used for anchoring the plate to bone. Some of the drawbacks with conventional locking plate systems include cross-threading of the locking screws with the threaded screw holes of the locking plate and misalignment of the locking screws with the screw holes. Thus, there remains a need for improved locking plate systems.

SUMMARY OF THE INVENTION

In one embodiment, a locking plate system preferably includes a locking plate having a top surface, a bottom surface, a screw hole extending through the locking plate having an inner diameter and internal threads, and a slot formed in the top surface of the locking plate adjacent the screw hole. The system desirably has a screw guide having a main body including an upper end and a lower end, and an attachment flange projecting from the lower end of the main body for insertion into the slot of the locking plate for securing the screw guide to the locking plate. The screw guide preferably includes a central opening that extends between the upper and lower ends of the main body, the central opening having an inner diameter that matches the inner diameter of the screw hole. The system desirably includes a locking screw having external threads extending along the length thereof, the external threads having an outer diameter that matches the inner diameter of the central opening of the screw guide, wherein the locking screw is insertable into the central opening of the screw guide for being directed into the screw hole.

In one embodiment, the locking screw desirably has a screw head and an elongated shaft, and the external threads are provided on both the screw head and the elongated shaft. In one embodiment, the external threads on the screw head and the elongated shaft have an outer diameter of about 3-5 mm, and more preferably about 3.5-4.5 mm. In one embodiment, the external threads on the screw head and the elongated shaft have the same pitch and size. In one embodiment, the external threads on the locking screw desirably have the same pitch as the internal threads of the screw hole.

In one embodiment, the slot is preferably a circular slot having an outer diameter that extends around the screw hole and the attachment flange comprises a circular ring having an outer diameter that matches the outer diameter of the circular slot. The circular ring is preferably insertable into the circular slot for securing the screw guide over the top surface of the locking plate and for aligning the central opening of the screw guide with the screw hole of the locking plate. In one embodiment, the screw guide preferably has a weakened region extending between the lower end of the main body and the circular ring for selectively detaching the circular ring from the main body.

The locking plate desirably has a plurality of screw holes extending therethrough. Each of the screw holes preferably has an inner diameter that matches the size of the inner diameter of the central opening of the screw guide and the outer diameter of the external threads on the locking screw. In one embodiment, the inner diameters of the screw holes, the inner diameter of the central opening of the screw guide, and the outer diameter of the external threads on the locking screw are between about 3-5 mm, and more preferably about 3.5-4.5 mm.

In one embodiment, the locking plate preferably includes a bushing incorporating the screw hole and the slot. The bushing may be pivotable to different angles relative to the top surface of the locking plate. In one embodiment, the locking plate is malleable and the screw hole may be bent to different angles relative to the top surface of the locking plate.

In one embodiment, after the screw guide flange is inserted into the locking plate slot for securing the screw guide to the locking plate, the external threads on the locking screw desirably closely engage the inner diameter of the central opening of the screw guide for maintaining the locking screw perpendicular to the top surface of the locking plate as the locking screw passes through the screw guide toward the screw hole of the locking plate.

In one embodiment, a locking plate system preferably includes a locking plate having a top surface, a bottom surface, a plurality of screw holes extending through the locking plate, each the screw hole having an inner diameter and internal threads, and circular slots formed in the top surface of the locking plate and surrounding each of the screw holes. The system desirably has a screw guide having a main body including an upper end and a lower end, and a circular attachment flange projecting from the lower end of the main body for insertion into the circular slots for securing the screw guide to the locking plate, whereby the screw guide includes a central opening that extends between the upper and lower ends of the main body, the central opening having a inner diameter that matches the inner diameters of the screw holes. The system desirably includes locking screws having external threads extending along the lengths thereof, the external threads having an outer diameter that matches the inner diameter of the central opening of the screw guide, whereby the locking screws are insertable into the central opening of the screw guide for being directed into the screw holes.

In one embodiment, the locking plate preferably includes a bushing incorporating one of the screw holes and one of the circular slots. The busing is preferably pivotable relative to the top surface of the locking plate for orienting the screw hole at different angles relative to the top surface of the plate.

In one embodiment, each of the locking screws has a screw head and an elongated shaft, and the external threads are provided on both the screw head and the elongated shaft. The external threads on the screw head and the elongated shaft preferably have the same pitch and size, and the external threads on the locking screws desirably have the same pitch as the internal threads of the screw holes.

In one embodiment, a locking plate system preferably has a locking plate having a top surface, a bottom surface, and screw holes extending from the top surface to the bottom surface of the locking plate, each screw hole having an inner diameter and internal threads, and a screw guide plate having a top surface, a bottom surface, and screw guide openings that extend between the top and bottom surfaces of the screw guide plate, each screw guide opening having an inner diameter that matches the inner diameter of the screw holes. A fastener preferably secures the screw guide plate to the locking plate so that the screw guide openings are aligned with the screw holes. The fastener may include at least one screw fastener extending through the screw guide plate and into the locking plate. The system preferably has locking screws having external threads extending along the lengths thereof. The external threads preferably have outer diameters that match the inner diameters of the screw guide openings, whereby the locking screws are insertable into the screw guide openings for directing the locking screws into the screw holes of the locking plate.

In one embodiment, the inner diameters of the screw holes, the inner diameters of the screw guide openings, and the outer diameters of the external threads of the locking screws are preferably between about 3-5 mm, and more preferably about 3.5-4.5 mm.

These and other preferred embodiments of the present invention will be described in more detail below.

BRIEF DESCRIPTION OF THE DRAWING

FIGS. 4A-4F show a method of using a locking screw guide and a locking screw for securing a locking plate to bone, in accordance with one embodiment of the present invention.

FIG. 5 shows a perspective view of Kirschner wire and a Kirschner wire guide, in accordance with one embodiment of the present invention.

FIG. 6 shows a front elevation view of a depth gauge used with the Kirschner wire of FIG. 5, in accordance with one embodiment of the present invention.

FIG. 7 shows a cannulated locking screw, in accordance with one embodiment of the present invention.

FIGS. 11A-11F show a malleable locking plate and a method of securing the locking plate to bone, in accordance with one embodiment of the present invention.

FIG. 12 shows a front elevation view of a locking bolt for securing a locking plate to bone, in accordance with one embodiment of the present invention.

FIG. 13 shows a front elevation view of a partially threaded locking screw, in accordance with one embodiment of the present invention.

DETAILED DESCRIPTION

Figure 1A:
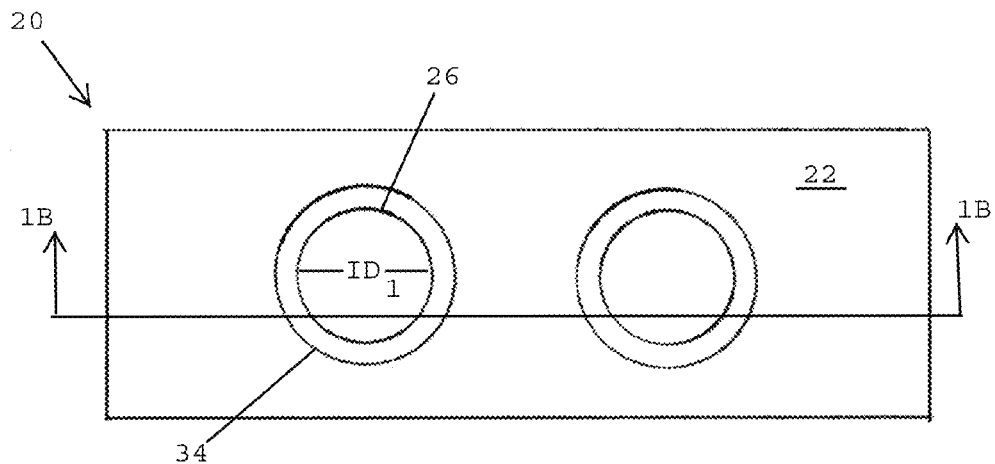
FIG. 1A shows a top plan view of a locking plate, in accordance with one embodiment of the present invention.
Figure 1B:
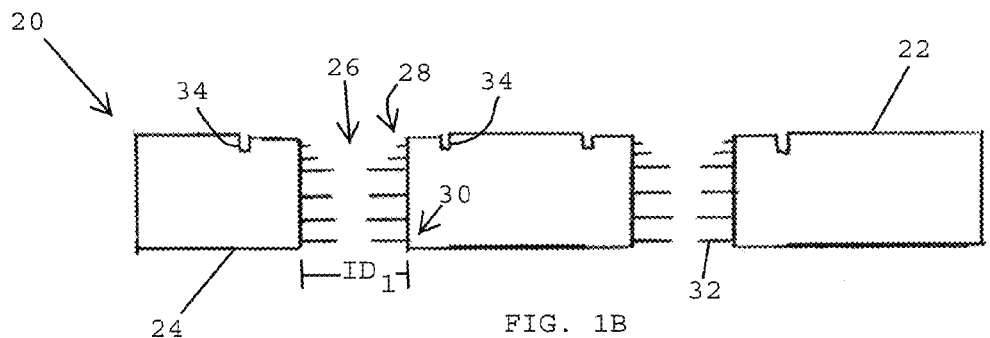
FIG. 1B shows a cross-sectional view of the locking plate of FIG. 1A taken along line 1B-1B thereof.

Referring to FIGS. 1A and 1B, in one embodiment, a locking plate 20 used during surgical procedures for repairing bone fractures preferably has a top surface 22 and a bottom surface 24 that is adapted for being positioned against a bone. The locking plate 20 preferably includes one or more screw holes 26 that extend through the plate 20. In one embodiment, the screw hole 26 defines an internal diameter $ID_1$ of about 3-5 mm and more preferably about 3.5-4.5 mm. Each screw hole 26 desirably includes an upper end 28 adapted to engage the head of a locking screw and a shaft receiving section 30 that extends from the upper end 28 to the bottom surface 24 of the plate 20. The upper end 28 and the shaft receiving section 30 of the screw hole 26 preferably include internally projecting threads 32 that are adapted to engage external threads on a locking screw. The threads at the upper end 28 of the screw hole 26 may be shorter than the threads within the shaft receiving section 30 of the screw hole 26.

In one embodiment, the locking plate 20 preferably includes a circular slot 34 that is formed in the top surface 22 of the plate 20 and that extends around the outer perimeter of the screw hole 26. The circular slot 34 is preferably adapted for seating a lower end of a locking screw guide, as will be described in more detail herein.

Figure 2:
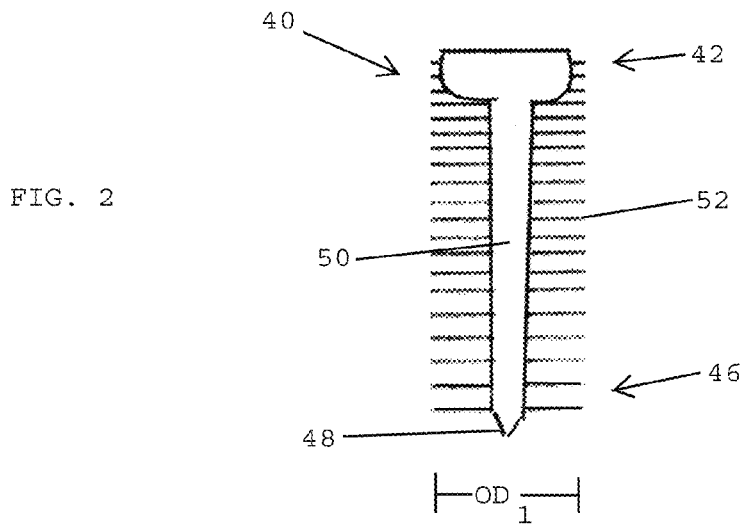
FIG. 2 shows a front elevation view of a locking screw having external threads extending along the length thereof, in accordance with one embodiment of the present invention.

Referring to FIG. 2, in one embodiment, a locking screw 40 is adapted for being inserted into the screw hole 26 of the locking plate 20. The locking screw 40 preferably has an upper end 42 including a screw head 44 and a lower end 46 including a pointed tip 48. The locking screw 40 preferably includes an elongated shaft 50 that extends from the underside of the screw head 44 to the pointed tip 48. The outer surface of the head 44 and the outer surface of the shaft 50 preferably have external threads 52 projecting therefrom. In one embodiment, the external threads 52 preferably have an outer diameter $OD_1$ of about 3-5 mm and more preferably about 3.5-4.5 mm. The external threads on the screw head 44 desirably have the same outer diameter and the same pitch as the external threads on the shaft 50. Although the length of the threads on the screw head may be shorter than the length of the threads on the shaft, the outer diameter of all of the threads is preferably the same along the entire length of the screw 40.

Figures 3A, 3B:
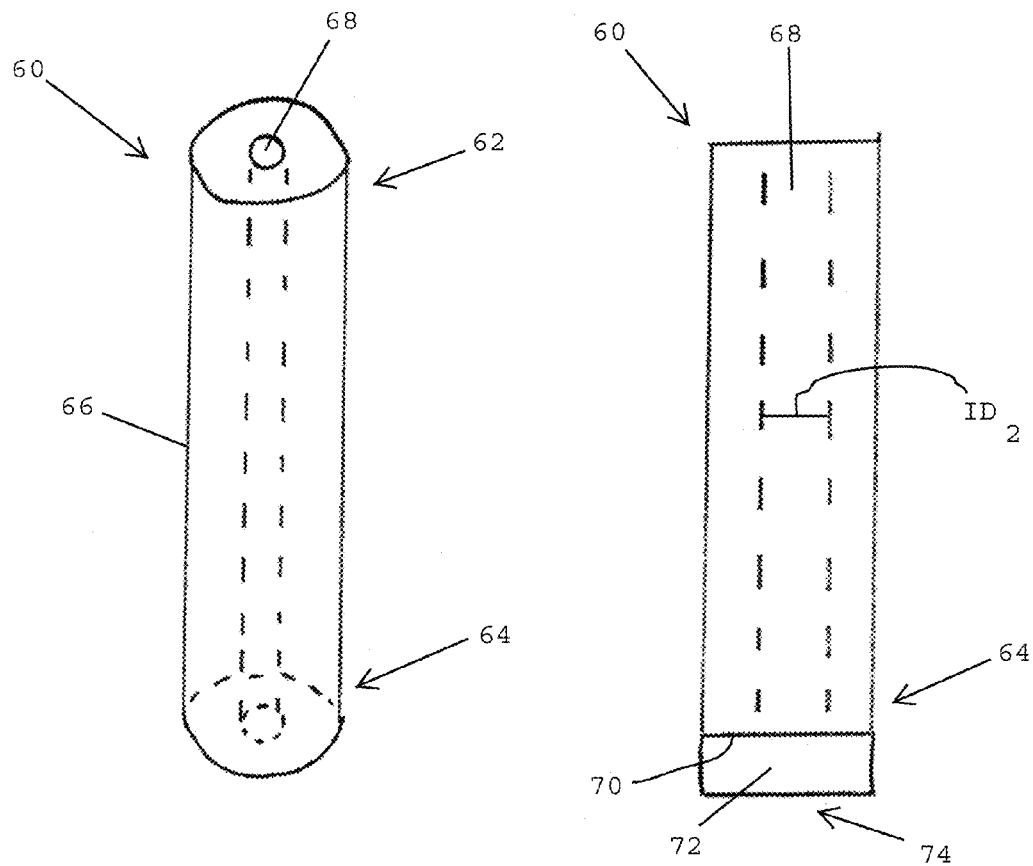
FIG. 3A shows a perspective view of a locking screw guide, in accordance with one embodiment of the present invention.
FIG. 3B shows a front elevation view of the locking screw guide shown in FIG. 3A.

Referring to FIG. 3A, in one embodiment, a screw guide 60 for use with the locking plate 20 of FIGS. 1A and 1B and the locking screw shown in FIG. 2 preferably has an upper end 62, a lower end 64 and an outer surface 66 that extends between the upper and lower ends. The screw guide 60 desirably has a central opening 68 that extends from the upper end 62 toward the lower end 64. The central opening 68 is preferably adapted to receive the locking screw 40 shown in FIG. 2 for guiding the locking screw through the screw guide and into the screw hole 26 of the locking plate shown in FIGS. 1A and 1B.

Referring to FIG. 3B, in one embodiment, the lower end 64 of the screw guide 60 preferably has a bottom wall 70 that traverses the central opening 68. The central opening 68 preferably has an internal diameter $ID_2$ that is preferably the same size as the inner diameter $ID_1$ of the screw hole 26 on the locking plate 20 (FIG. 1B) and the outer diameter $OD_1$ of the external threads 52 on the locking screw 40 (FIG. 2). In one embodiment, the lower end 64 of the screw guide 60 is perforated around the outer perimeter thereof in the vicinity of the ring portion 72 to facilitate tearing away an upper end of the screw guide and leaving the ring portion within the circular slot 34 of the locking plate 20. In one embodiment, the upper end of the screw guide 60 is preferably removed after a locking screw has been advanced through the screw guide 60 and threaded into a screw hole 26 on the locking plate 20.

Figure 3C:
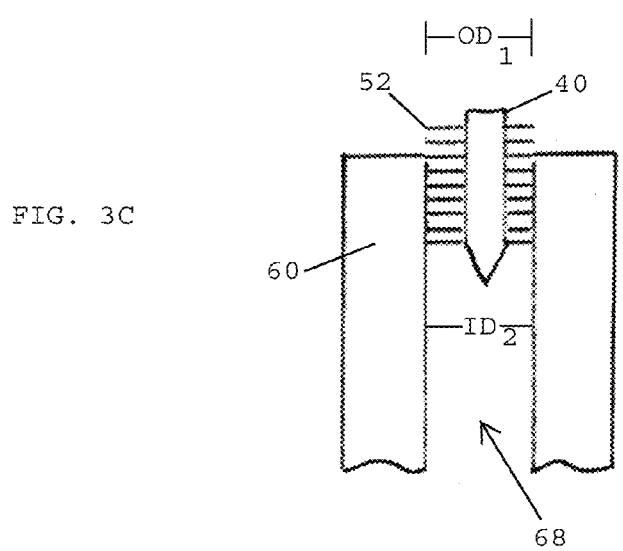
FIG. 3C shows a lower end of the locking screw of FIG. 2 being advanced through a central opening of the locking screw guide shown in FIGS. 3A and 3B.

FIG. 3C shows the outer diameter $OD_1$ of the external threads 52 on the locking screw 40 closely matching the inner diameter $ID_2$ of the central opening 68 of the screw guide 60 for maintaining proper alignment of the locking screw 40 as it is guided through the screw guide and toward the screw hole 26 in the locking plate 20 (FIG. 1B). The lower end 64 of the screw guide 60 preferably includes a circular ring 72 that defines a circular opening 74. The circular ring 72 is adapted for being inserted into the circular slot 34 formed in the top surface 22 of the locking plate 20.

Referring to FIG. 4A, in one embodiment, the circular ring 72 at the lower end 64 of the screw guide 60 is aligned with the circular slot 34 on the locking plate 20. Referring to FIG. 4B, in one embodiment, the circular ring 72 at the lower end 64 of the screw guide 60 is inserted into the circular slot 34 formed in the top surface 22 of the locking plate 20 so that the central opening of the screw guide is aligned with the screw hole. The central opening 68 of the screw guide 60 preferably has an inner diameter $ID_2$ that is the same as the internal diameter $ID_1$ of the screw hole 26 extending through the locking plate 20.

Referring to FIG. 4C, in one embodiment, the bottom surface 24 if the locking plate 20 is positioned atop a bone B with the screw hole 26 of the locking plate 20 and the central opening 68 of the screw guide 60 aligned with one another. The locking plate 20 has external threads 52 having an outer diameter $OD_1$ that matches the inner diameter $ID_2$ of the central opening 68 of the screw guide 60, which, in turn, matches the inner diameter $ID_1$ of the screw hole 26 in the locking plate 20.

Referring to FIG. 4D, in one embodiment, the locking screw 40 is inserted into the central opening 68 of the screw guide 60. The close match between the outer diameter $OD_1$ of the threads 52 on the locking screw 40 and the inner diameter $ID_2$ of the central opening 68 of the screw guide 60 maintains proper alignment of the locking screw 40 with the screw hole 26 in the locking plate 20 and ensures that the locking screw 40 does not toggle and/or shift as it moves through the central opening 68 of the screw guide 60 and toward the screw hole 26.

When the tip 48 of the locking screw 40 passes through the internal threads 32 at the upper end 28 of the screw hole 26, the external threads 52 on the locking screw 40 mesh with the internal threads 32 of the screw hole 26.

Figure 4E:
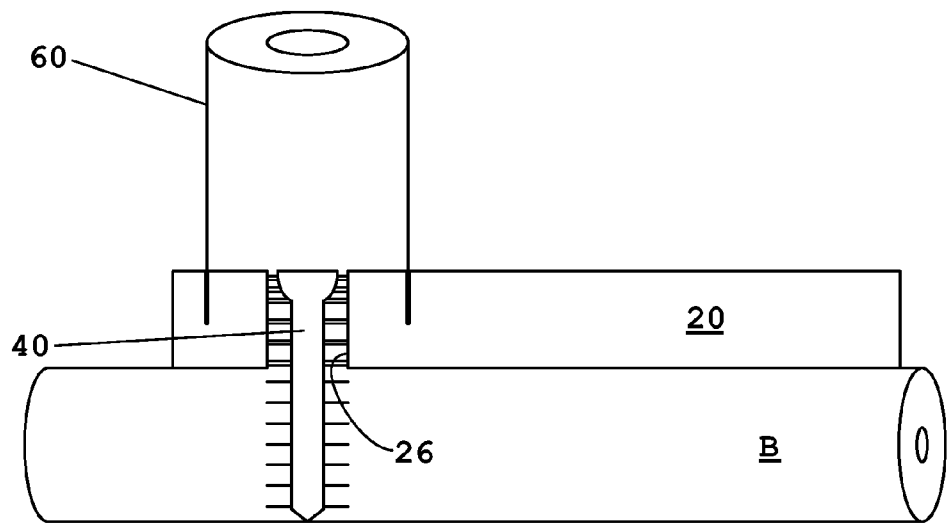

Referring to FIG. 4E, the locking screw 40 is preferably fully threaded into the threads of the screw hole 26. The internal diameter of the screw guide matches the outer diameter of the threads on the locking screw 40, which prevents the locking screw from cross-threading. The alignment of the inner and outer diameters also desirably ensures that the locking screw will be guided into the locking screw hole 26 at the proper orientation required to avoid cross-threading and improper alignment within the bone B. Thus, the present invention eliminates cross-threading and ensures that the locking screw 40 will pass through the screw hole 26 of the locking plate 20 and into the bone at a preferred orientation.

Figure 4F:
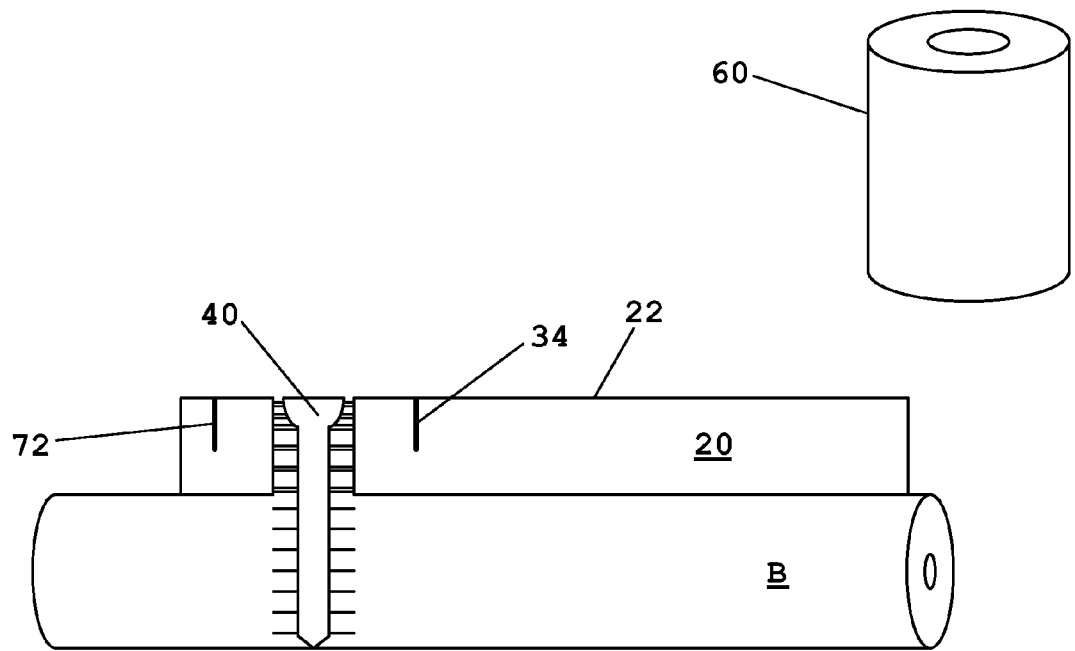

FIG. 4F shows the locking screw 40 fully inserted into the screw hole 26 of the plate 20 and anchored in the bone B and for firmly securing the plate to the bone B. Referring to FIG. 4F, in one embodiment, after the locking screw 40 has been fully inserted into the locking plate 20, the upper end of the screw guide 60 may be removed (e.g. torn away), which leaves the circular ring 72 at the lower end of the screw guide remaining inside the circular slot 34 formed in the top surface 22 of the locking plate 20.

Referring to FIG. 5, in one embodiment, a Kirschner wire 80, commonly referred to as a K-wire, is used in conjunction with a K-wire guide 82 having a cylindrical outer shaft 84 and a central opening 86 extending along the length of the shaft 84. The cylindrical outer shaft 84 preferably has an outer diameter $OD_3$ that matches the inner diameter $ID_2$ of the screw guide 60 (FIG. 4B).

Referring to FIG. 6, in one embodiment, a depth gauge 86 may be used for determining how far the K-wire 80 has been inserted into the bone B. The depth gauge 86 desirably has a central opening 88 that extends from an open, lower end 90 toward a closed upper end 92. The depth gauge 86 preferably includes a scale 94 that has indicia for measuring how far the K-wire 80 (FIG. 5) has been inserted into bone.

Referring to FIG. 7, in one embodiment, a cannulated screw 95 preferably has a head 96, a shaft 98, and a cannulated opening 100 that extends from the head 96 to a distal tip 102. The cannulated screw 94 preferably has external threads 104 that extend from the head 96 to the tip 102. The external threads 104 on both the head 96 and the shaft 98 of the cannulated screw 95 have the same outer diameter $OD_4$. The outer diameter $OD_4$ of the threads 104 preferably match the inner diameter $ID_2$ of the central opening 68 of the screw guide 60 (FIG. 4B). The close fit between the outer diameter $OD_4$ of the threads 104 and the inner diameter $ID_2$ of the central opening of the screw guide 60 ensures that the cannulated screw 95 will be maintained in proper alignment and orientation relative to the internal threads of the screw hole 26 in the locking plate 20. As will be described in more detail herein, the cannulated screw 94 is preferably advanced into the screw hole 26 and the bone B for securing the locking plate 20 to the bone B. The K-wire may then be removed.

Figure 8A:
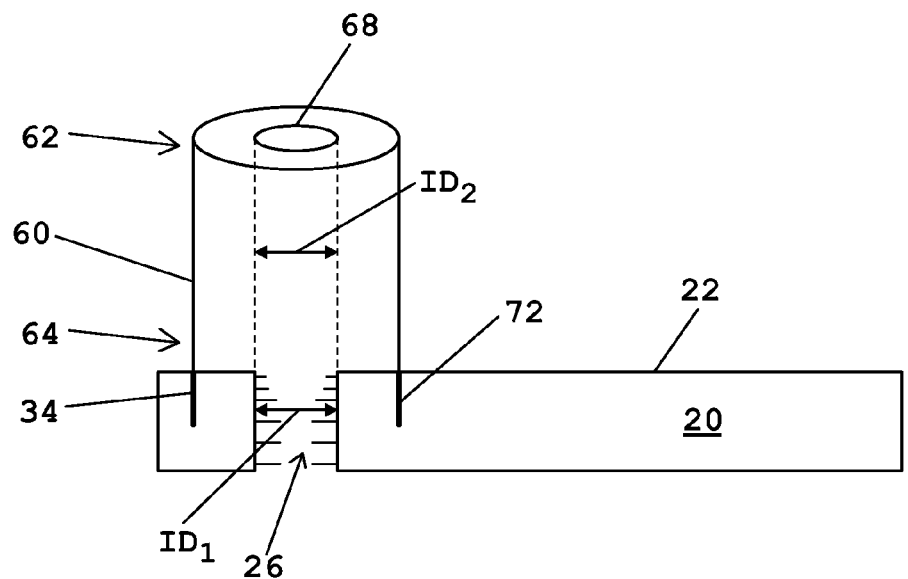
FIGS. 8A-8D show a method of securing a locking plate to bone using the cannulated locking screw of FIG. 7, in accordance with one embodiment of the present invention.

Referring to FIG. 8A, in one embodiment, a locking plate 20 having a screw hole 26 and a screw guide 60 pre-assembled therewith. The circular ring 72 at the lower end 64 of the screw guide 60 is inserted into the circular slot 34 formed in the top surface 22 of the locking plate 20. The screw guide 60 desirably includes the central opening 68 that extends from an upper end 62 to a lower end 64 of the screw guide. The central opening 68 of the screw guide has an inner diameter $ID_2$ that is the same as the inner diameter $ID_1$ of the screw hole 26.

Figure 8B:
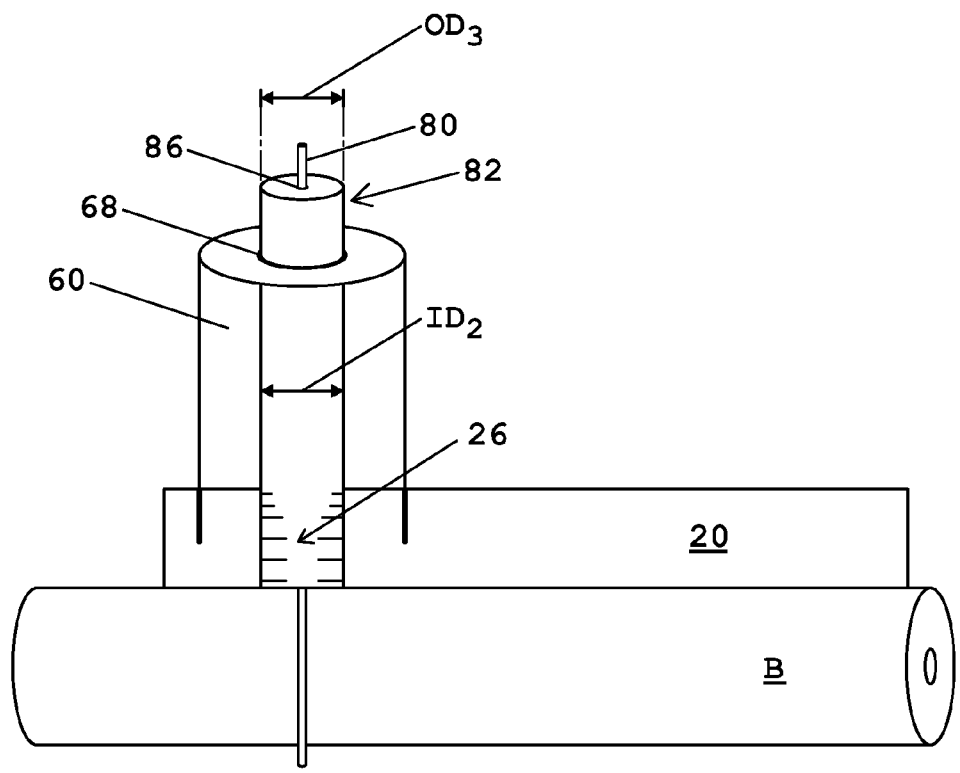

Referring to FIG. 8B, the K-wire guide 82 may be inserted into the central opening 68 of the screw guide 60. The outer diameter $OD_3$ of the K-wire guide 82 matches the inner diameter $ID_2$ of the screw guide 60. The lower end of the K-wire guide 82 preferably advances through the screw hole 26 until the lower end of the K-wire guide abuts against the bone B. The K-wire 80 is preferably passed through the central opening 86 of the K-wire guide 82 and inserted into the bone B to a desired. Fluoroscopic pictures may be taken of the bone B and the K-wire 80 to ensure that the K-wire is properly positioned in the bone.

Figure 8C:
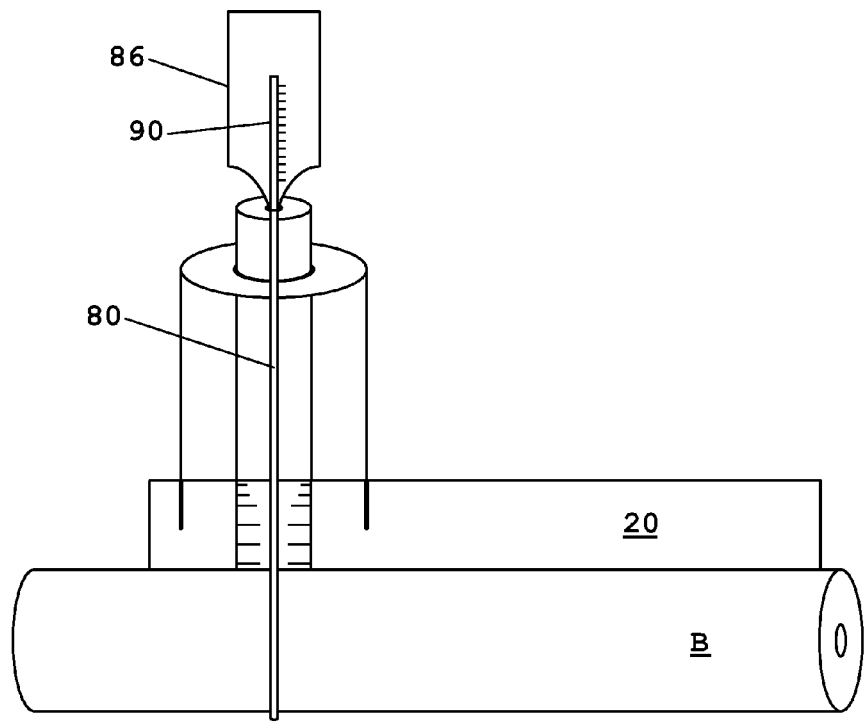
Figure 8D:
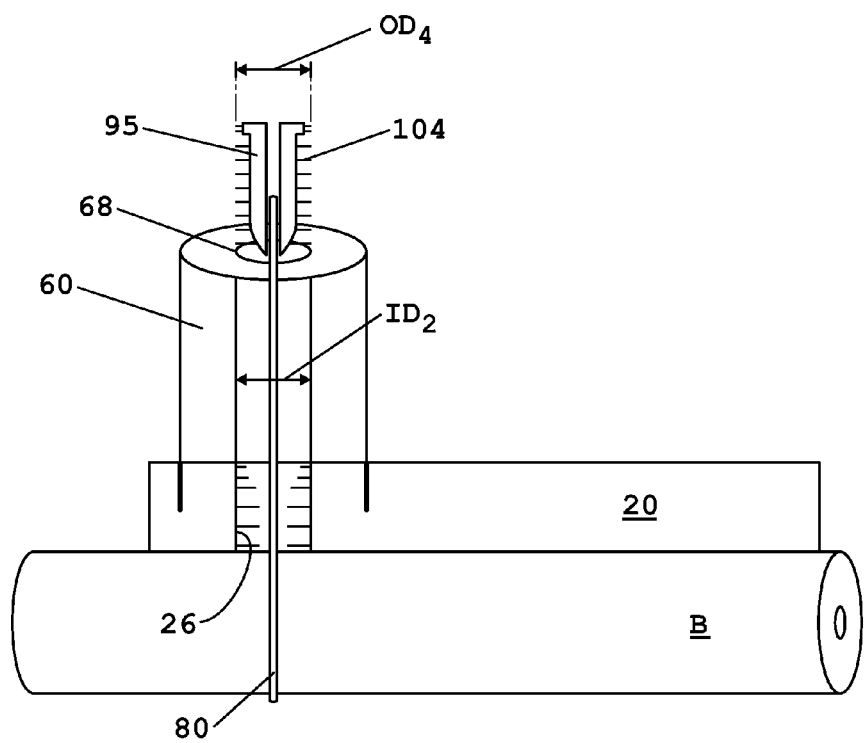

Referring to FIG. 8C, after the K-wire 80 has been inserted into bone B, the depth gauge 86 is preferably slid over the top of the K-wire 80 for measuring how far the K-wire has been inserted into the bone B. The measurement determined on the scale 90 desirably enables medical personnel to determine the length of the threaded screw to be used for properly securing the locking plate 20 to the bone B. After it has been determined that the K-wire is properly positioned, and after property length for the locking screw has been determined, the depth gauge 86 may be removed.

In one embodiment, the cannulated screw 95 is preferably passed over the K-wire 80. The outer diameter $OD_4$ of the threads 104 preferably matches the inner diameter $ID_2$ of the central opening 68 of the screw guide 60. The close fit between the outer diameter $OD_4$ of the threads 104 and the inner diameter $ID_2$ of the central opening of the screw guide 60 ensures that the cannulated screw 95 will be maintained in proper alignment and orientation relative to the screw hole 26 in the plate 20. The cannulated screw 95 is preferably advanced into the screw hole 26 and the bone B for securing the locking plate 20 to the bone B. The K-wire is then removed.

Figure 9A:
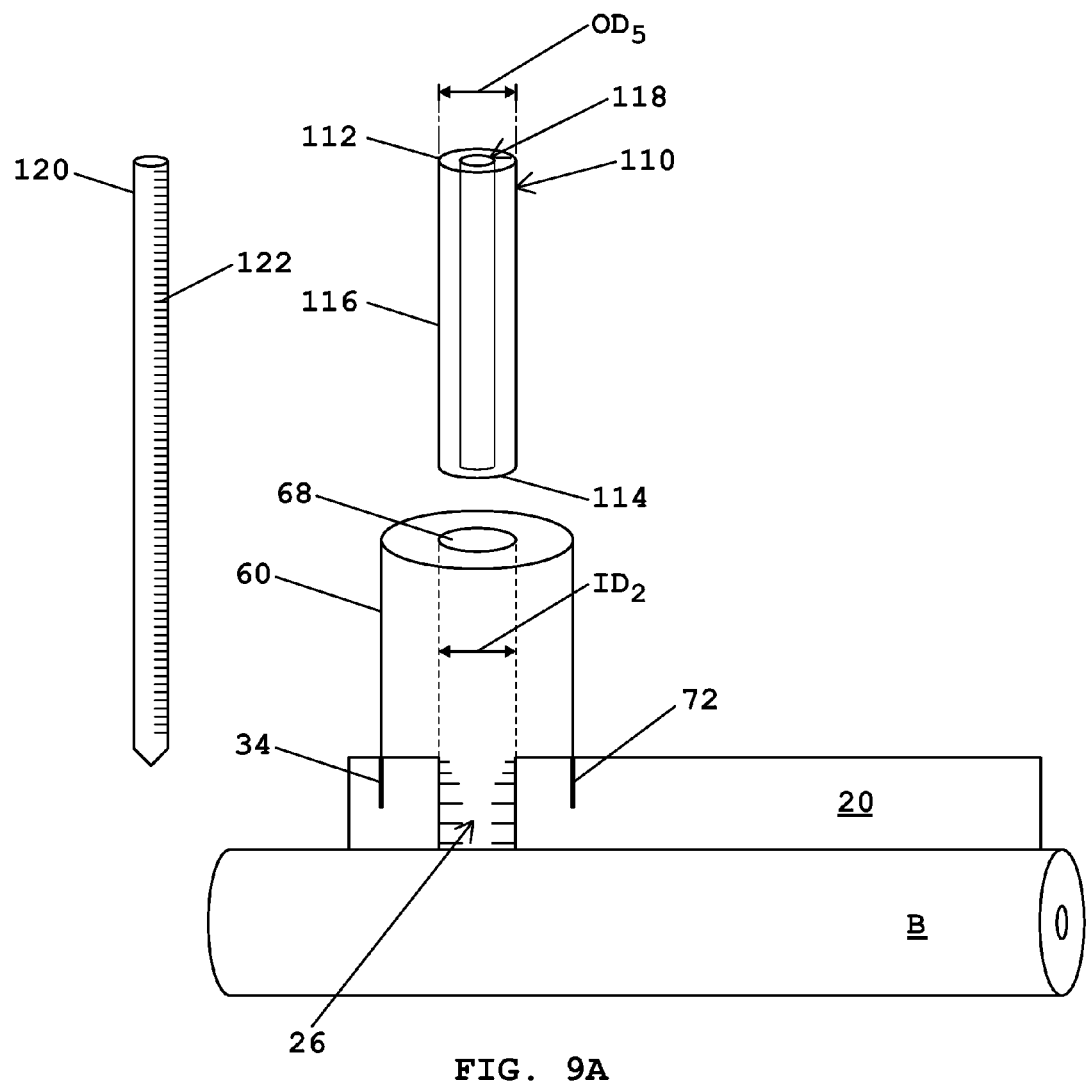
FIGS. 9A-9F show a method of securing a locking plate to bone using a locking screw, in accordance with one embodiment of the present invention.

Referring to FIG. 9A, in one embodiment, a drill guide 110 has an upper end 112, a lower end 114 and a cylindrical outer shaft 116 that extends between the upper and lower ends. The drill guide 110 preferably includes a central opening 118 that extends from the upper end 112 to the lower end 114 thereof. The outer surface 116 of the drill guide 110 preferably has an outer diameter $OD_5$ that matches the inner diameter $ID_2$ of the central opening 68 of the locking screw guide 60 (FIG. 3B). The drill guide 110 is preferably used for guiding advancement of a drill bit 120 through the screw hole 26 and into bone. In one embodiment, the drill bit 120 preferably has a scale 122 provided thereon that extends along the length thereof for determining how far the drill bit 120 has been advanced into the bone B.

In one embodiment, a locking plate 20 includes a screw hole 26 extending therethrough. The locking plate 20 has a circular slot 34 formed in the top surface 22 for securing the screw guide 60 to the locking plate 20. A circular ring 72 at a lower end of a screw guide 60 is inserted into the circular slot 34 for securing the screw guide to the locking plate. The screw guide 60 has a central opening 68 having an inner diameter $ID_2$ that substantially matches the outer diameter $OD_5$ of the drill guide 110.

Figure 9B:
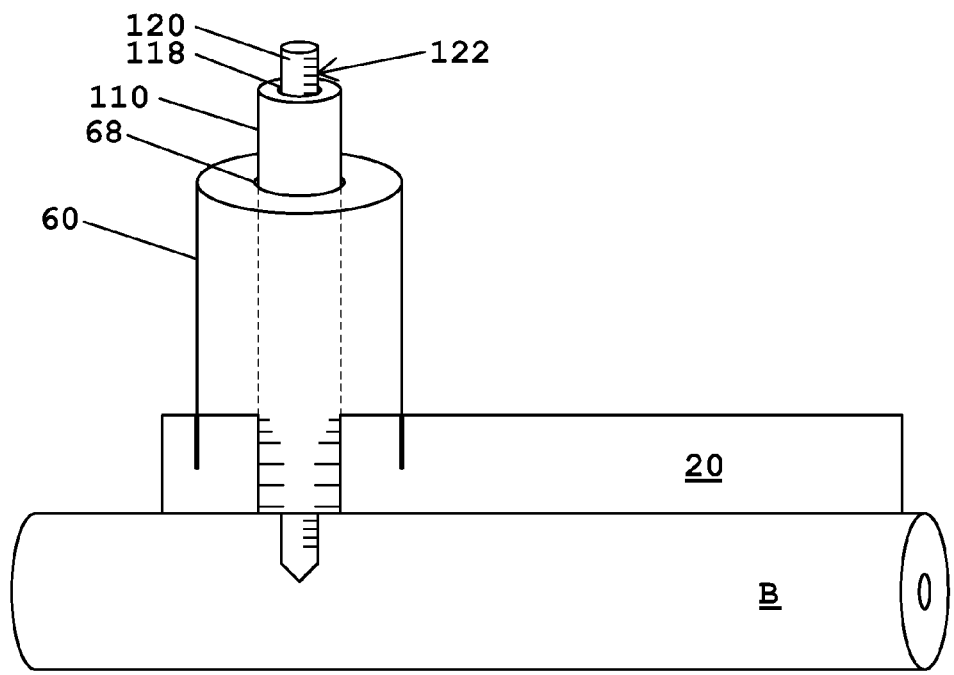

Referring to FIG. 9B, the drill guide 110 is desirably inserted into the central opening 68 of the screw guide 60 and advanced toward the bone B until the lower end of the drill guide 110 abuts against the bone. The drill bit 120 is then advanced through the drill guide opening 118 for drilling a hole in the bone B. The scale 122 on the drill bit 120 preferably indicates how far the drill bit has been advanced into the bone B, which may be utilized for determining the proper length of a locking screw.

Figure 9C:
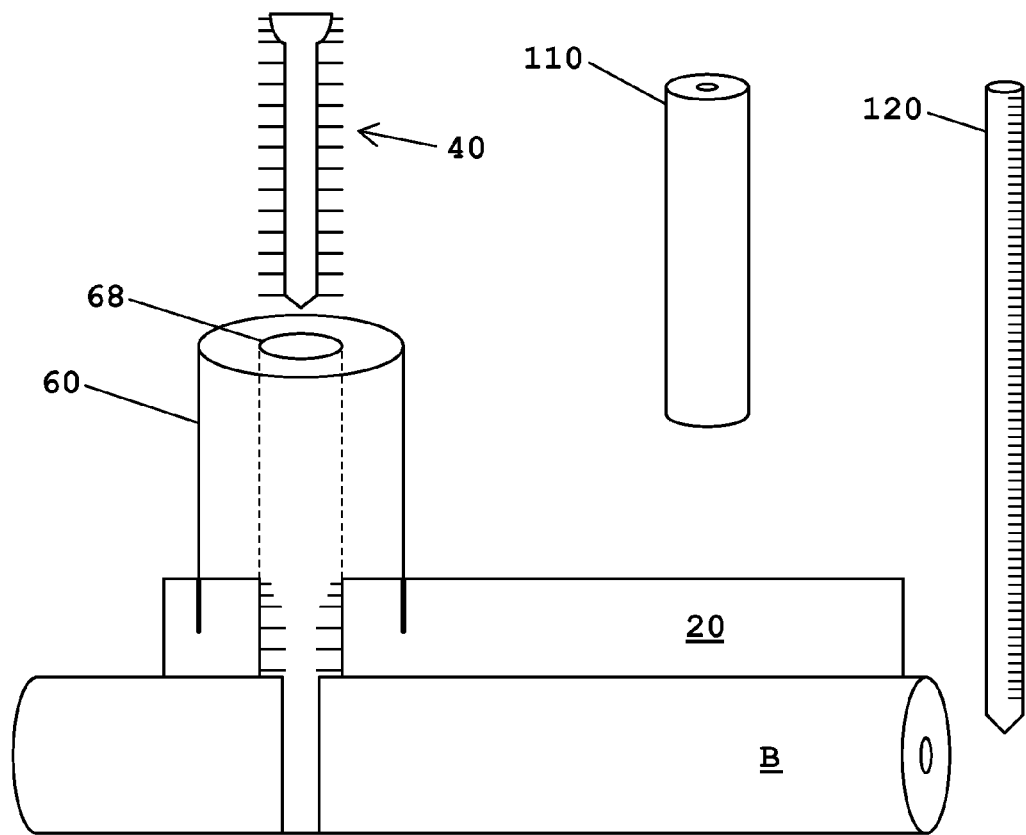
Figure 9D:
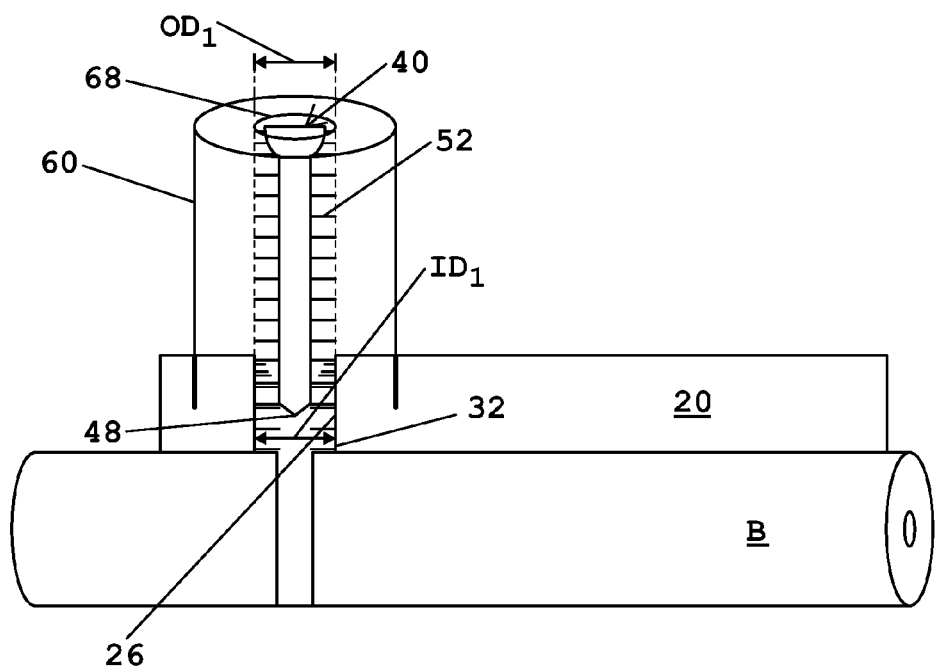

Referring to FIG. 9C, after a hole has been drilled in the bone B, the drill bit 120 and the drill guide 110 are preferably removed from the central opening 68 of the screw guide 60 so that the locking screw 40 may be inserted into the screw guide 60. Referring to FIG. 9D, the locking screw 40 having external threads 52 is passed into the central opening 68 of the screw guide 60. The outer diameter $OD_1$ of the external threads 52 preferably matches the inner diameter $ID_2$ of the central opening 68 and the inner diameter $ID_1$ of the screw hole 26. The locking screw 40 is preferably threaded into the internal threads 32 of the screw hole 26. As the locking screw 40 is further advanced into the screw hole 26 of the locking plate 20, the tip 48 of the locking screw 40 desirably advances into the bone B.

Figure 9E:
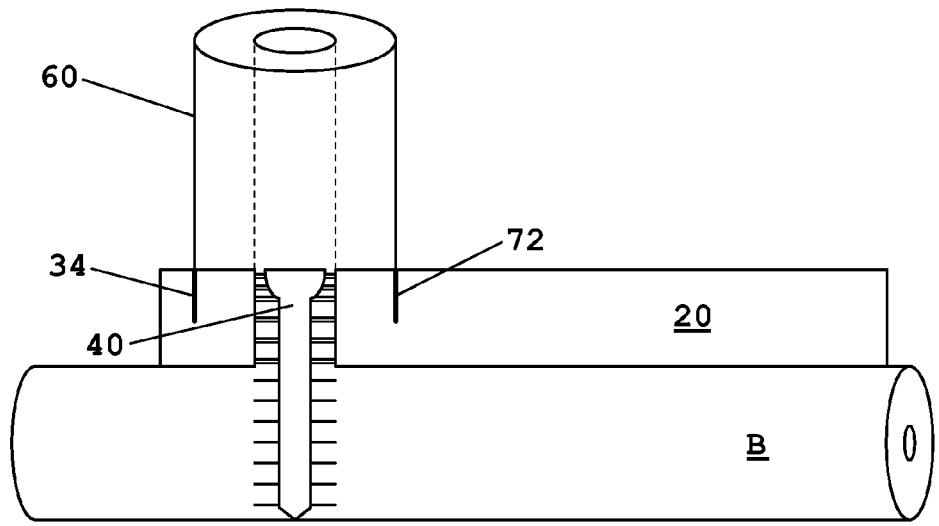
Figure 9F:
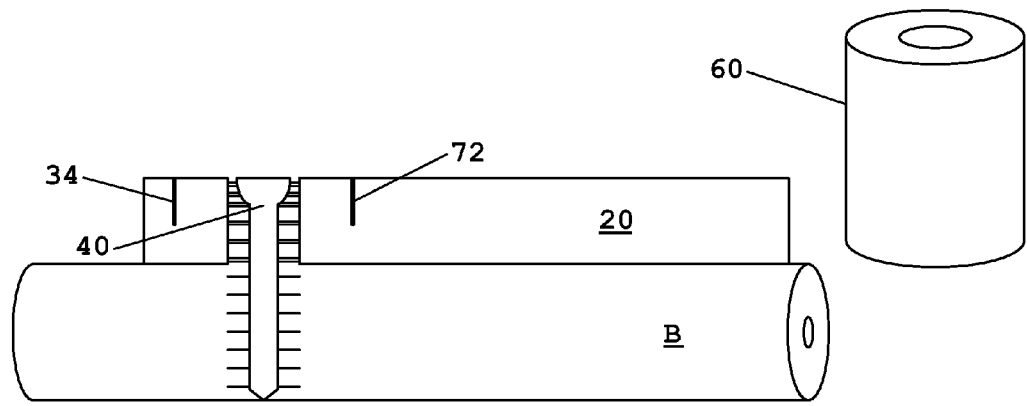

Referring to FIGS. 9E and 9F, after the locking screw 40 has been fully inserted into the bone B for locking the locking plate 20 to the bone, the upper end of the screw guide 60 is desirably removed (e.g. broken off) from the locking plate 20.

The circular ring 72 at the lower end of the screw guide 60 remains disposed within the circular slot 34 of the plate 20.

Figure 10A:
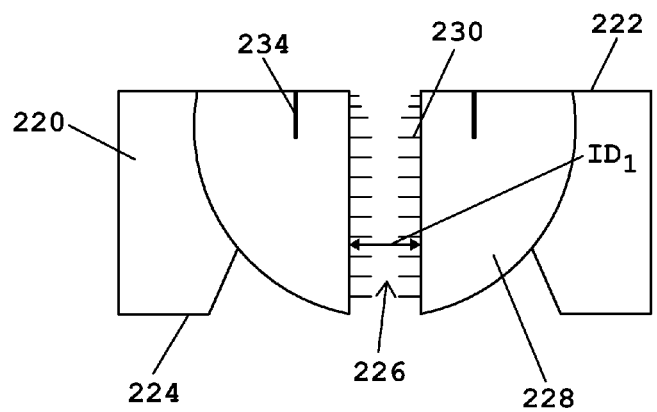
FIGS. 10A-10G show a locking plate having a pivoting bushing and a method of securing the locking plate to bone using a locking screw, in accordance with one embodiment of the present invention.

Referring to FIG. 10A, in one embodiment, a locking plate 220 preferably includes a top surface 222, a bottom surface 224, and a screw hole 226 that extends through a pivoting bushing 228 that is adapted to pivot to selected angles relative to the locking plate 20. The pivoting bushing 228 preferably includes internal threads 230 that extend along the length of the bushing 228. The screw hole 226 preferably has an inner diameter $ID_1$ that matches the outer diameter $OD_1$ of the threads on the locking screw 50 (FIG. 2).

The pivoting bushing 228 desirably includes a circular slot 234 that is formed in a top surface thereof. The circular slot 234 surrounds the screw hole 226 and preferably pivots simultaneously with the bushing 228.

Figure 10B:
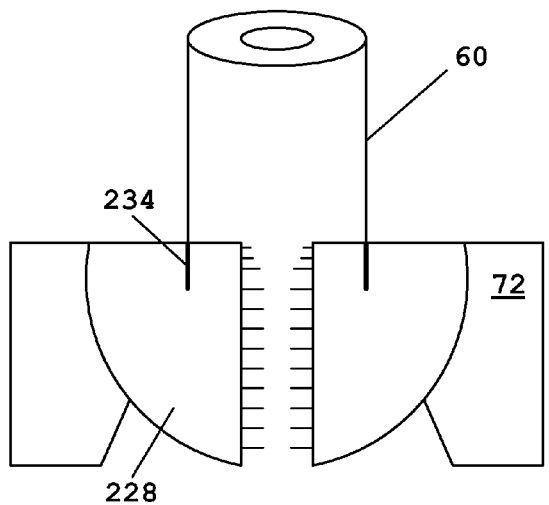

Referring to FIG. 10B, in one embodiment, the circular ring 72 at the lower end of the screw guide 60 is preferably inserted into the circular slot 234 provided on the pivoting bushing 228 for securing the screw guide 60 to the bushing 228.

Figure 10C:
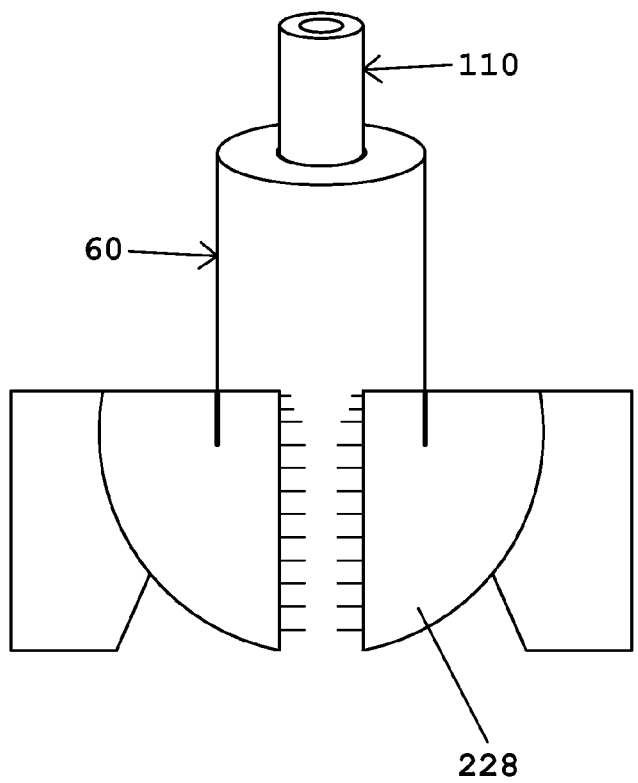
Figure 10D:
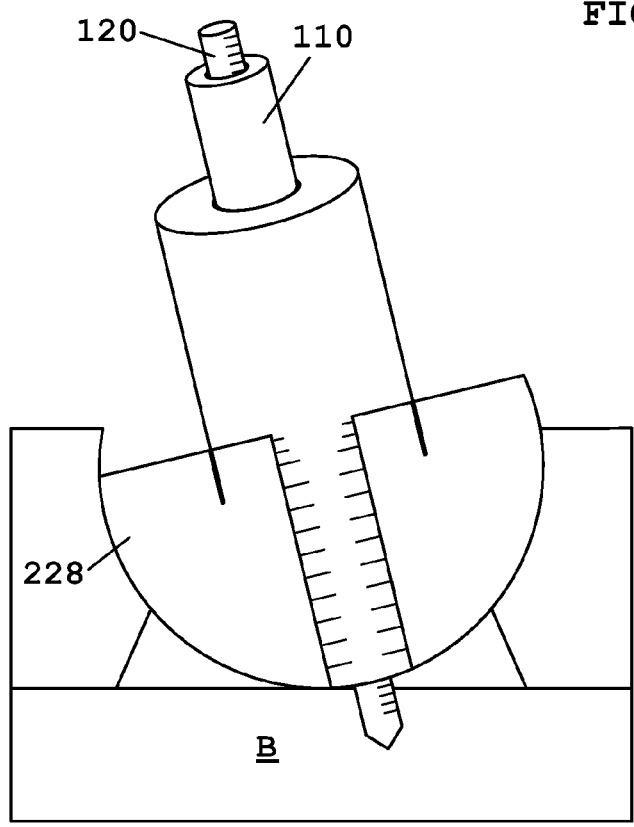

Referring to FIG. 10C, a drill guide 110 may be inserted into the central opening 68 of the screw guide 60. The screw guide 60 and the drill guide 110 are preferably used for pivoting the bushing 228 to a desired angle. While maintaining the bushing 228 at a desired angle as shown in FIG. 10D, a drill bit 120 may be advanced through a central opening in the drill bit guide 110 for drilling a hole into bone.

Figure 10E:
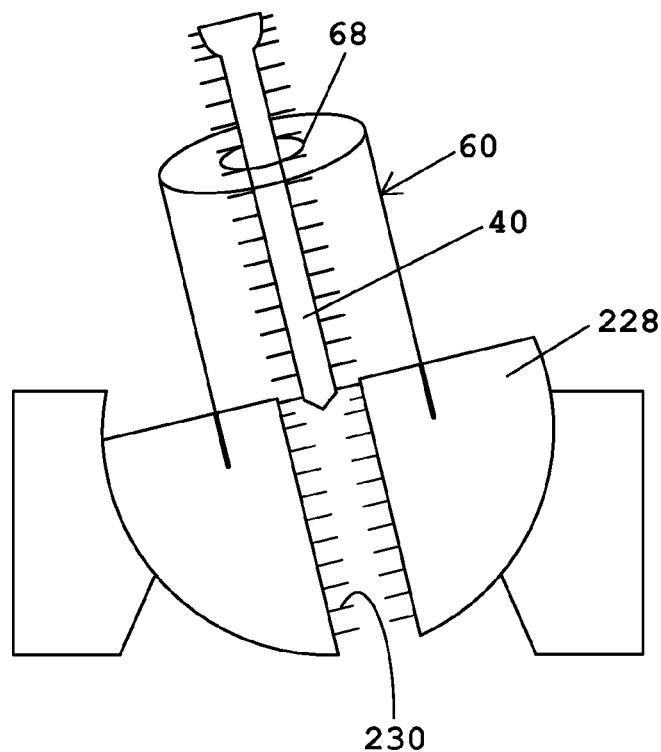

Referring to FIG. 10E, a locking screw 40 may then be advanced through the central opening 68 of the screw guide 60 for engaging the internal threads of the bushing 228. The external threads on the locking screw 40 preferably have an outer diameter $OD_1$ that matches the inner diameter $ID_2$ of the central opening 68 of the screw guide 60, and the internal diameter of the screw hole 226 in the bushing 228.

Figure 10F:
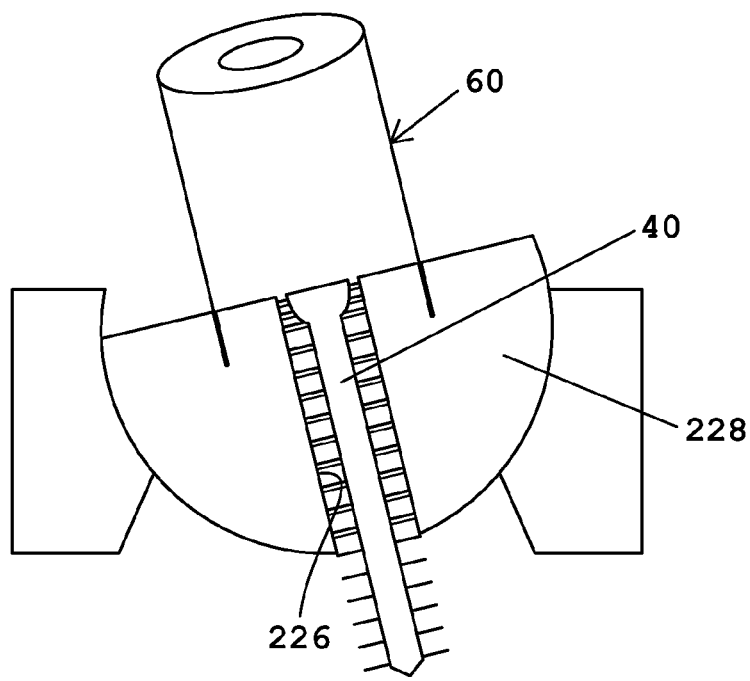
Figure 10G:
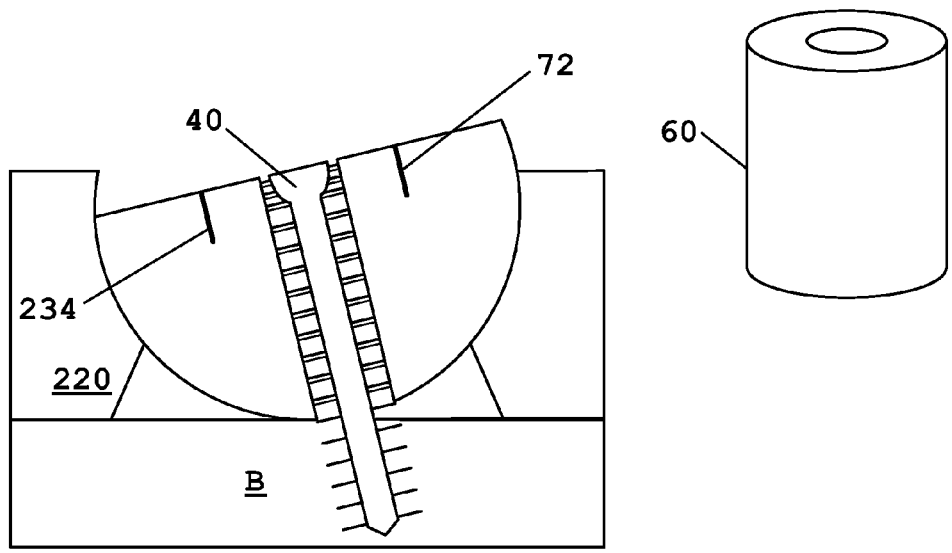

Referring to FIG. 10F, the screw guide 60 properly aligns and orients the locking screw 40 as it advances toward the screw hole 226 for threading the external threads on the locking screw into the internal threads of the pivotable bushing 228. Referring to FIG. 10G, after the locking screw 40 has been tightened for securing the locking plate 220 to bone B, the upper end of the screw guide 60 may be removed from engagement with the bushing 228. The circular ring 72 at the lower end of the screw guide 60 desirably remains disposed within the circular slot 234 of the bushing 228.

Figure 11A:
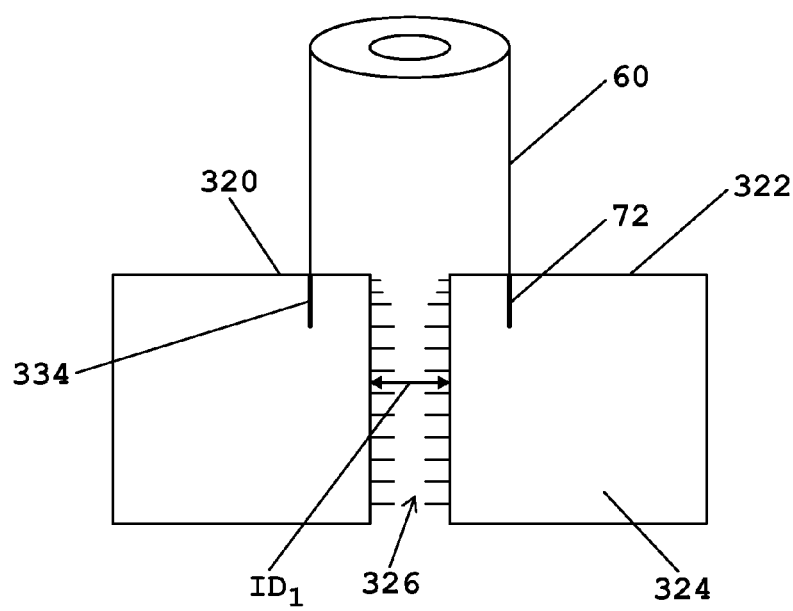

Referring to FIG. 11A, in one embodiment, a locking plate 320 is made of a malleable material. The locking plate 320 preferably includes a top surface 322, a bottom surface 324 and a screw hole 326 extending from the top surface to the bottom surface. The screw hole 326 has an internal diameter $ID_1$ that matches the outer diameter $OD_1$ of the external threads on a locking screw 40 (FIG. 2).

The locking plate 320 preferably has a circular slot 334 formed in the upper surface 322 thereof. The circular slot 334 is adapted to receive a circular ring 72 projecting from a lower end of a screw guide 60.

Figure 11B:
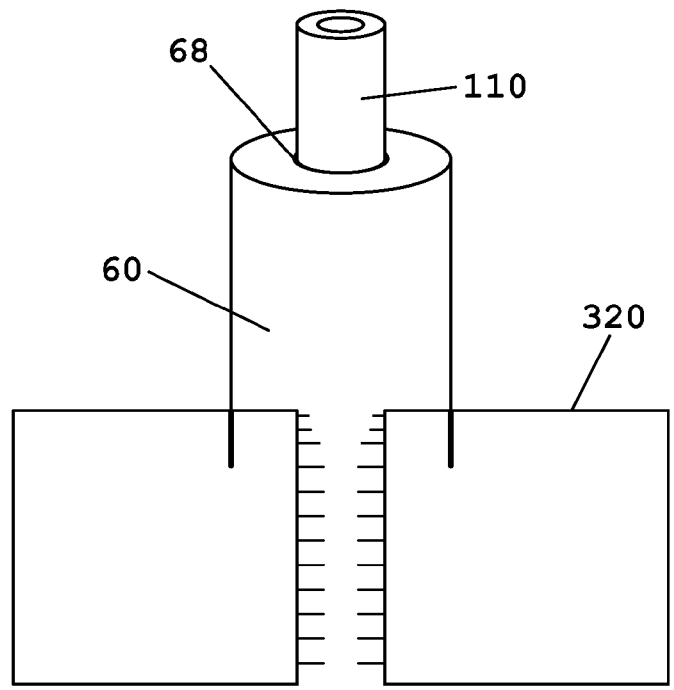

Referring to FIG. 11B, the screw guide 60 may be used for drilling a hole in bone. In one embodiment, a drill guide 110 is inserted into the central opening 68 of the screw guide 60. The drill guide 110 has a central opening for guiding advancement of a drill bit through the drill guide, through the locking plate 320 and into the bone B.

Figure 11C:
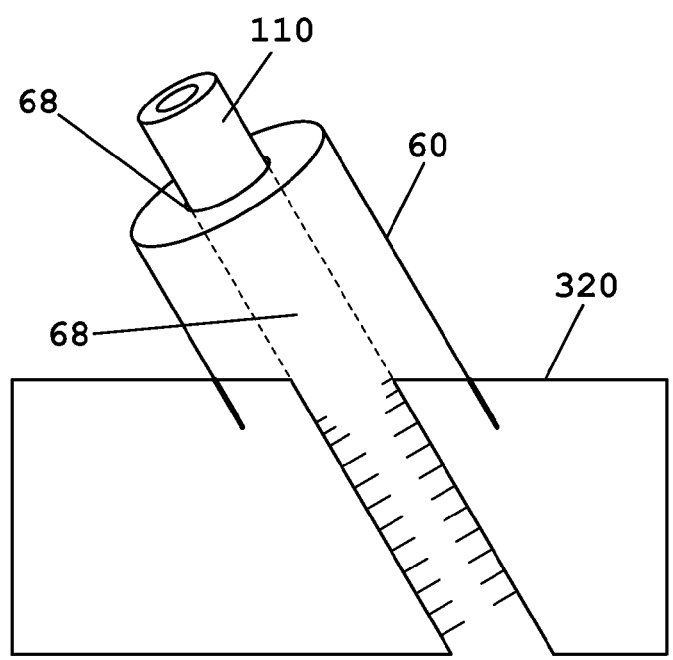

Referring to FIG. 11C, prior to using a drill bit for drilling into bone, and with the drill guide 110 inserted into the central opening 68 of the screw guide 60, the screw guide 60 is grasped for bending the malleable locking plate 320 and orienting the central opening 60 of the screw guide 60 at a particular angle. The drill guide 110 is preferably maintained inside the screw guide 60 when bending the plate 320 so that the central opening 68 of the screw guide 60 does not deform during the bending operation.

Figure 11D:
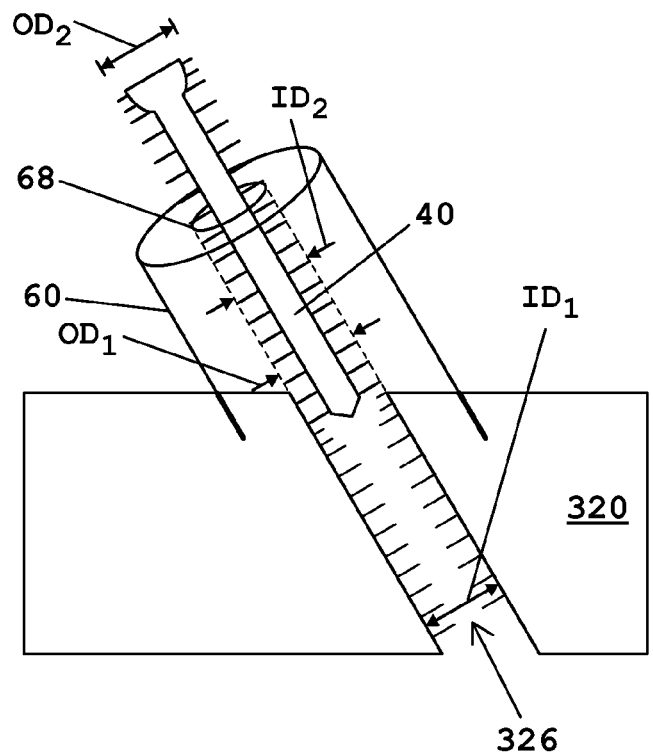
Figure 11E:
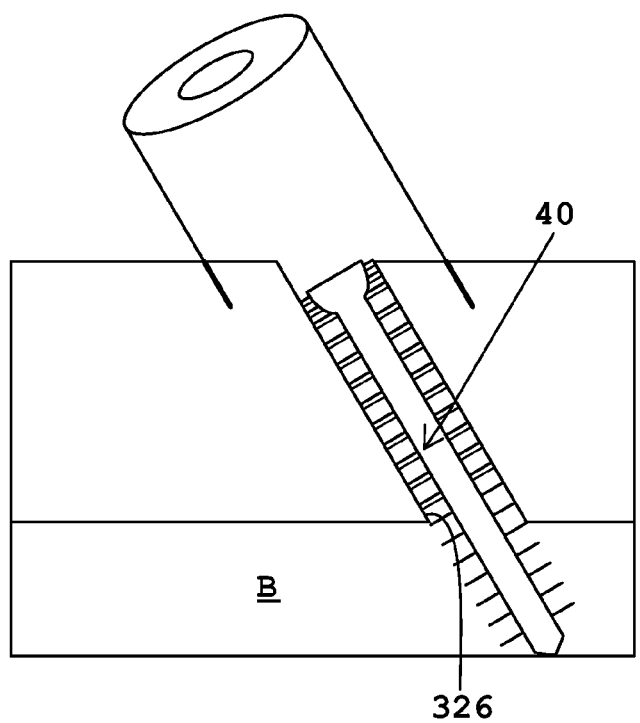

Referring to FIG. 11D, after the hole is drilled in the bone, the drill bit and the drill guide are desirably removed and a locking screw 40 may be inserted into the central opening 68 of the screw guide 60. The outer diameter $OD_1$ of the external threads on the locking screw 40 preferably match the inner diameter $ID_2$ of the central opening 68 for maintaining the screw properly aligned with the internal threads of the screw hole 326. The outer $OD_1$ of the external threads on the locking screw 40 also preferably match the inner diameter $ID_1$ of the screw hole 326 in the locking plate 320.

FIG. 11F shows the locking screw 40 after being fully inserted into internal threads of the screw hole 326 and the bone B. Referring to FIG. 11F, after the locking screw 40 has been tightened, the upper portion of the screw guide 60 may be torn away and disposed of, leaving the circular ring 72 of the screw guide disposed within the circular slot 324.

Referring to FIG. 12, in one embodiment, a locking bolt 440 has an upper end 442 and a lower end 444. The upper end 442 includes a head 446. The locking bolt 440 includes a cylindrical shaft 448 that extends between the head 446 and the lower end 444 thereof. The outer surface of the head 446 has external threads 450 having an outer diameter $OD_1$ that matches the inner diameter $ID_2$ of the central opening 68 of the screw guide 60 (FIG. 3B). The outer diameter of the cylindrical shaft 448 preferably matches the outer diameter $OD_1$ of the external threads 450 on the locking screw.

FIG. 13 shows a locking screw 540 having an upper end 542 and a lower end 544. The upper end 542 includes a head 546. The locking screw 540 includes an elongated shaft 548 that extends between the head 546 and the lower end 544. The head 546 of the locking screw 540 has a first set of external screw threads 550A. The shaft 548 includes a second set of external screw threads 550B that extend to the lower end 544 of the screw 540. A central section of the shaft 548 has no external threads. The outer diameter $OD_1$ of the threads 550A on the head 546 matches the outer diameter $OD_1$ of the threads 550B on the lower portion of the shaft.

Figure 14A:
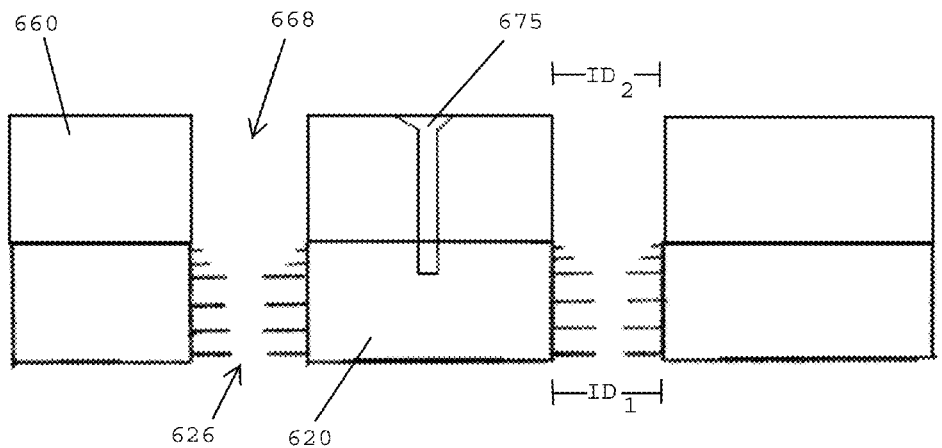
FIG. 14A shows a locking plate system including a screw guide plate having screw guide openings aligned with screw holes on a locking plate, in accordance with one embodiment of the present invention.
Figure 14B:
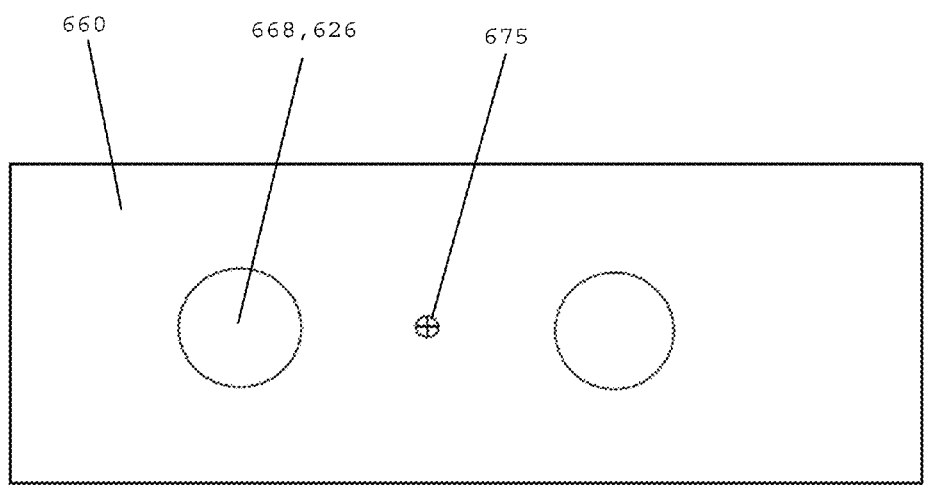
FIG. 14B shows a top plan view of the locking plate system of FIG. 14A.

Referring to FIGS. 14A and 14B, in one embodiment, a locking plate system preferably includes a locking plate 620 with screw holes 526 having respective inner diameters $ID_1$, and internal threads extending toward the centers of the respective screw holes 626. A screw guide plate 660 is secured over a top surface of the locking plate 620 using a fastener 675. The screw guide plate 660 includes screw guide openings 668 having respective inner diameters $ID_2$. The screw guide openings 668 are preferably aligned with the screw holes 626. Although the present invention is not limited by any particular theory of operation, it is believed that the screw guide plate having a plurality of screw guide openings may be used for efficiently and accurately guiding a plurality of locking screws into each of the respective screw holes 626. Although two screw holes and screw guide holes are shown, other embodiments may include three or more screw holes and screw guide holes. More than one fastener 675 may also be used.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A locking plate system comprising:
   a locking plate having a top surface, a bottom surface, a screw hole extending through said locking plate having an inner diameter and internal threads, and a circular slot formed in said top surface of said locking plate adjacent said screw hole, wherein said circular slot is concentric with said screw hole;
   a screw guide having a main body including an upper end and a lower end, and an attachment flange projecting from said lower end of said main body for insertion into said circular slot of said locking plate for securing said screw guide to said locking plate, wherein said screw guide includes a central opening that extends between said upper and lower ends of said main body, said central opening having an inner diameter that matches the inner diameter of said screw hole; and
   a locking screw having external threads extending along the length thereof, said external threads having an outer diameter that matches the inner diameter of said central opening of said screw guide and the inner diameter of said screw hole in said locking plate, wherein said locking screw is insertable into said central opening of said screw guide for being directed into said screw hole, wherein said locking screw has a screw head and an elongated shaft, wherein the length of said external threads projecting from said screw head are shorter than the length of said external threads projecting from said elongated shaft, and wherein said external threads on said screw head and said external threads on said elongated shaft have the same outer diameter, wherein said circular slot has an outer diameter that extends around said screw hole and said attachment flange comprises a circular ring having an outer diameter that matches the outer diameter of said circular slot, and wherein the inner diameter of said central opening of said screw guide is smaller than the inner diameter of said attachment flange.

2. The locking plate system as claimed in claim 1, wherein said internal threads adjacent said top surface of said locking plate are shorter than said internal threads adjacent said bottom surface of said locking plate, and wherein the inner diameter of said screw hole remains constant between said top and bottom surfaces of said locking plate.

3. The locking plate system as claimed in claim 2, wherein said external threads on said screw head and said elongated shaft have an outer diameter of 3-5 mm.

4. The locking plate system as claimed in claim 2, wherein said external threads on said screw head and said elongated shaft have the same pitch and size.

5. The locking plate system as claimed in claim 4, wherein said external threads on said locking screw have the same pitch as said internal threads of said screw hole.

6. The locking plate system as claimed in claim 1, wherein said circular ring is insertable into said circular slot for securing said screw guide over said top surface of said locking plate and for aligning said central opening of said screw guide with said screw hole of said locking plate, and wherein said bottom wall of said screw guide overlies said top surface of said locking plate when said attachment flange is inserted into said circular slot.

7. The locking plate system as claimed in claim 6, where said screw guide has a weakened region extending between said lower end of said main body and said circular ring for selectively detaching said circular ring from said main body.

8. The locking plate system as claimed in claim 1, wherein said locking plate has a plurality of screw holes extending therethrough, each said screw hole having an inner diameter that remains constant between said top and bottom surfaces of said locking plate and that is the same size as the size of the inner diameter of said central opening of said screw guide and the outer diameter of said external threads on said locking screw.

9. The locking plate system as claimed in claim 8, wherein the inner diameters of said screw holes, the inner diameter of said central opening of said screw guide, and the outer diameter of said external threads on said locking screw are between 3-5 mm.

10. The locking plate system as claimed in claim 1, further comprising a bushing incorporating said screw hole and said circular slot, wherein said bushing is pivotable to different angles relative to said top surface of said locking plate, wherein said bushing does not extend below said bottom surface of said locking plate, and wherein said attachment flange projecting from the lower end of said screw guide is insertable into said circular slot on said bushing so that said screw guide pivots simultaneously with said bushing.

11. The locking plate as claimed in claim 1, wherein said locking plate is malleable, and wherein said screw hole may be bent to different angles relative to said top surface of said locking plate.

12. The locking plate system as claimed in claim 1, wherein after said screw guide flange is inserted into said locking plate circular slot for securing said screw guide to said locking plate, said external threads on said locking screw closely engage the inner diameter of said central opening of said screw guide for maintaining said locking screw perpendicular to said top surface of said locking plate as said locking screw passes through said screw guide toward said screw hole of said locking plate.

13. A locking plate system comprising:
a locking plate having a top surface, a bottom surface, a plurality of screw holes extending through said locking plate, each said screw hole having an inner diameter and internal threads, and circular slots formed in said top surface of said locking plate and surrounding each of said screw holes, wherein each said circular slot is concentric with, extends around, and is spaced from one of said screw holes;
a screw guide having a main body including an upper end and a lower end, and a circular attachment flange projecting from said lower end of said main body for insertion into said circular slots for securing said screw guide to said locking plate, wherein said screw guide includes a central opening that extends between said upper and lower ends of said main body, said central opening having an inner diameter that matches the inner diameters of said screw holes; and locking screws having external threads extending along the lengths thereof, said external threads having an outer diameter that matches the inner diameter of said central opening of said screw guide and the inner diameters of said screw holes, wherein said locking screws are insertable into said central opening of said screw guide for being directed into said screw holes, wherein each said locking screw has a screw head and an elongated shaft, wherein the length of said external threads projecting from said screw head are shorter than the length of said external threads projecting from said elongated shaft, and wherein said external threads on said screw head and said external threads on said elongated shaft have the same outer diameter.

14. The locking plate system as claimed in claim 13, wherein said locking plate further comprises a bushing incorporating one of said screw holes and one of said circular slots, wherein said busing is pivotable relative to said top surface of said locking plate for orienting said screw hole at different angles relative to said top surface of said plate, and wherein said pivotable bushing does not extend below said bottom surface of said locking plate.

15. The locking plate system as claimed in claim 13, wherein each of said locking screws has a screw head and an elongated shaft, and wherein said external threads are provided on both said screw head and said elongated shaft.

16. The locking plate system as claimed in claim 15, wherein said inner diameters of said screw holes remain constant between said top and bottom surfaces of said locking plate, wherein said external threads on said screw head and said elongated shaft have the same pitch and size, and wherein said external threads on said locking screws have the same pitch as said internal threads of said screw holes.

17. The locking plate system as claimed in claim 13, wherein said circular attachment flange comprises a circular ring having an outer diameter that matches the outer diameters of said circular slots, and wherein the inner diameter of said central opening of said screw guide is smaller than the inner diameter of said attachment flange.

* * * * *